US012133667B2

(12) United States Patent
Nadim et al.

(10) Patent No.: US 12,133,667 B2
(45) Date of Patent: Nov. 5, 2024

(54) SELF-CONTOURING PLATE SYSTEM FOR BONE FRACTURES

(71) Applicant: Orthopedic Designs North America, Inc., Tampa, FL (US)

(72) Inventors: Yasser Nadim, Somerset, KY (US); Lance Fagan, Tampa, FL (US)

( * ) Notice: Subject to any disclaimer, the term of this patent is extended or adjusted under 35 U.S.C. 154(b) by 369 days.

(21) Appl. No.: 17/805,492

(22) Filed: Jun. 6, 2022

(65) Prior Publication Data
US 2023/0127954 A1 Apr. 27, 2023

Related U.S. Application Data

(63) Continuation-in-part of application No. 17/508,813, filed on Oct. 22, 2021, now abandoned.

(51) Int. Cl.
*A61B 17/80* (2006.01)
*A61B 17/86* (2006.01)
*A61B 17/00* (2006.01)

(52) U.S. Cl.
CPC ...... *A61B 17/8061* (2013.01); *A61B 17/8014* (2013.01); *A61B 17/8057* (2013.01); *A61B 17/8085* (2013.01); *A61B 17/8605* (2013.01); *A61B 2017/00477* (2013.01)

(58) Field of Classification Search
CPC . A61B 17/80; A61B 17/8023; A61B 17/8061; A61B 17/8066; A61B 17/8085
See application file for complete search history.

(56) References Cited

U.S. PATENT DOCUMENTS

| 6,060,641 | A | * | 5/2000 | Manolidis | A61F 2/2803 128/898 |
| 8,591,551 | B2 | * | 11/2013 | Miller | A61B 17/7001 606/264 |
| 8,685,022 | B2 | | 4/2014 | Lorenz et al. | |
| 8,821,552 | B2 | * | 9/2014 | Reitzig | A61B 17/7059 606/282 |
| 9,636,157 | B2 | | 5/2017 | Medoff | |
| 9,750,538 | B2 | | 9/2017 | Soffiatti et al. | |
| 10,206,713 | B2 | | 2/2019 | Olsen et al. | |
| 2013/0274803 | A1 | * | 10/2013 | Noordeen | A61B 17/7013 606/256 |
| 2020/0289271 | A1 | * | 9/2020 | Nedrud | A61F 2/2803 |

FOREIGN PATENT DOCUMENTS

CN 111588455 8/2020

* cited by examiner

Primary Examiner — Larry E Waggle, Jr.
(74) Attorney, Agent, or Firm — Larson & Larson; Justin P. Miller; Frank Liebenow

(57) ABSTRACT

The self-contouring plate system for bone fractures allows a surgeon to bridge a bone fracture, primarily in bones of complex shape where the use of plates or screws is difficult. The self-contouring plate is formed from a series of similar or identical rigid elements, the elements able to bend and rotate with respect to each other. This flexibility is initially helpful as the surgeon contours the device to the shape of the bone. When the desired shape is reached, the elements are locked into place. The length of device is adjusted by adding or removing elements, much like a necklace. Each element of the self-contouring plate includes a ball that extends away from a body, a cavity for receiving the ball of the neighboring plate, and a screw to compress the ball within the cavity.

18 Claims, 10 Drawing Sheets

SELF-CONTOURING PLATE SYSTEM FOR BONE FRACTURES

CROSS-REFERENCE TO RELATED APPLICATION

This application is a continuation-in-part of U.S. patent application Ser. No. 17/508,813, filed Oct. 22, 2021, titled Self-contouring plate for bone fractures.

FIELD

This invention relates to the field of treating bone fractures and more particularly to a device for treating a complex bone fracture.

BACKGROUND

The treatment of complex bone fractures has moved beyond the antiquated treatments of full-body casts and traction.

Instead, the use of screws and plates helps surgeons to fix fractures in position, allowing the patient to regain partial mobility while the bone mends.

But the use of mechanical fracture supports, such as plates, is complicated by bones with complex shapes, such as the pelvis.

Current methods require the surgeon to contour, or bend, a plate during surgery, the plate intended to match the contour of the patient's bone.

This contouring is difficult and imperfect and can result in fractures that are only partially reduced. And imperfect contouring can cause loss of reduction obtained prior to applying the plate. The result is increased healing time and decreased patient mobility.

What is needed is a device that is contoured to the bone, the device then locked into shape and affixed to the bone.

SUMMARY

The self-contouring plate system for bone fractures allows a surgeon to bridge a bone fracture, primarily in bones of complex shape where the use of plates or screws is difficult.

The self-contouring plate system is formed from a series of similar or identical rigid elements, the elements able to bend and rotate with respect to each other. This flexibility is initially helpful as the surgeon contours the device to the shape of the bone. When the desired shape is reached, the elements are locked into place.

The length of device is adjusted by adding or removing elements, much like a necklace. Each element of the self-contouring plate includes a ball that extends away from a body, a cavity for receiving the ball of the neighboring plate, and one or more screws to compress the ball within the cavity.

Each element can rotate in three directions—swivel left and right, or yaw; tilt forward and backward, or pitch; and rotate about its centerline, or roll. This freedom of rotation is created by a ball-and-socket connection that joins each element to the next. When the desired arrangement and angles are reached, the ball-and-socket joint is fixed in position by compression of the socket. Compression of the socket is created by one or more compression screws. Restated, the ball-and-socket joint has both a locked position or condition, and an unlocked position or condition—a compressed position and an uncompressed position.

The ball-and-socket connection allows for a full range of motion. The preferred embodiment has the ability to swivel in 45 degrees of yaw, tilt between 45- and 90-degrees of pitch, and rotate in 360 degrees of roll.

One or more screw holes in each element allow placement of bone screws, fixing the device to the underlying bone.

The entire device is intended for permanent internal implantation, directly against the bone. The device does not protrude through muscle or skin, and does not have elements that remain external to the body.

The centerline of each element of the device is preferably consistent, with the centerline of the ball matching that of the centerline of the body. When installation is complete, there are no protruding elements that could cause discomfort by aggravating the surrounding tissues. Stated differently, in the preferred embodiment the thickness of the device is substantially consistent, without protruding elements. The ball and socket are preferably positioned at opposite ends of the body.

The self-contouring plate is strengthened by being positioned against the surface of the bone. The plates and connections are directly against the surface of the bone, avoiding rotational moments that would increase the force against the plates. This is in contrast to the prior art devices, which were placed partially outside the patient's skin, resulting in traumatic and uncomfortable pins that passed through the patient's bone and muscle. The prior art placed the points of rotation away from the bone, thus requiring a thicker mechanism to compensate for the resulting rotational forces.

The self-contouring plate includes a solid ball, without a through-hole for a fixation screw. The result is a stronger ball connection with more material. The ball is preferably spherical, with the only interruption to its surface being the neck that connects the ball to the body of the plate.

Additionally, by using a solid ball, the greatest range of movement is possible. Requiring placement of a fastener through the ball limits angular rotation of the ball because the hole in the ball must line up with a second hole for receipt of the fastener.

This additional range of motion is helpful in complex fractures, such as fractures of the pelvis and acetabulum.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
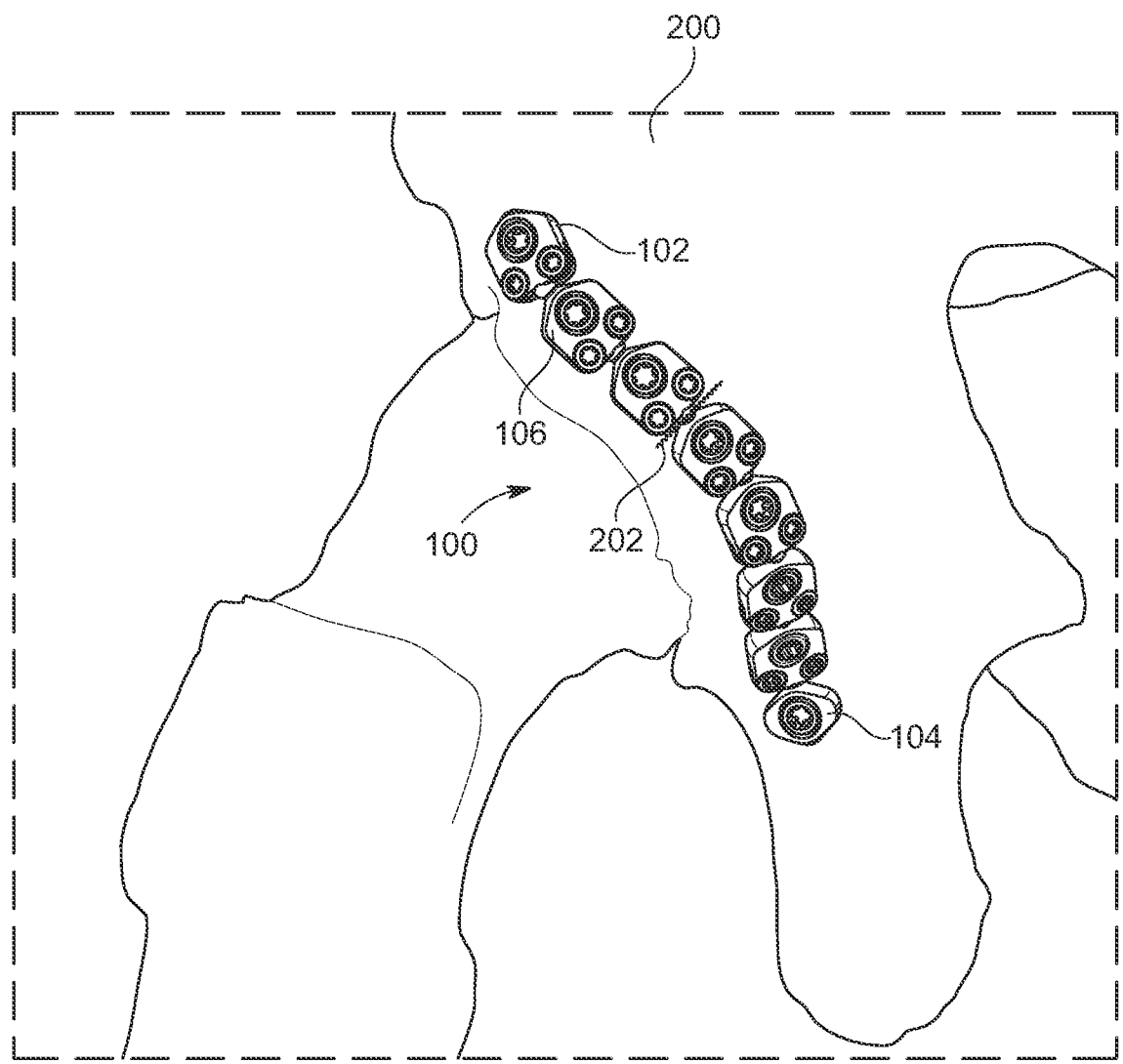
FIG. 1 illustrates a first installed view of the self-contouring plate.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a first installed view of the self-contouring plate is shown.

The self-contouring plate system 100 is shown installed against the pelvis 200, bridging a fracture line 202. The self-contouring plate system 100 is preferably formed from a head plate 102, one or more central plates 106, and a tail plate 104.

The pelvis 200 is curved, but the self-contouring plate system 100 compensates, following the curvature.

The surgeon can choose the quantity of central plates 106 based on the desired length of the resulting self-contouring plate system 100.

Figure 2:
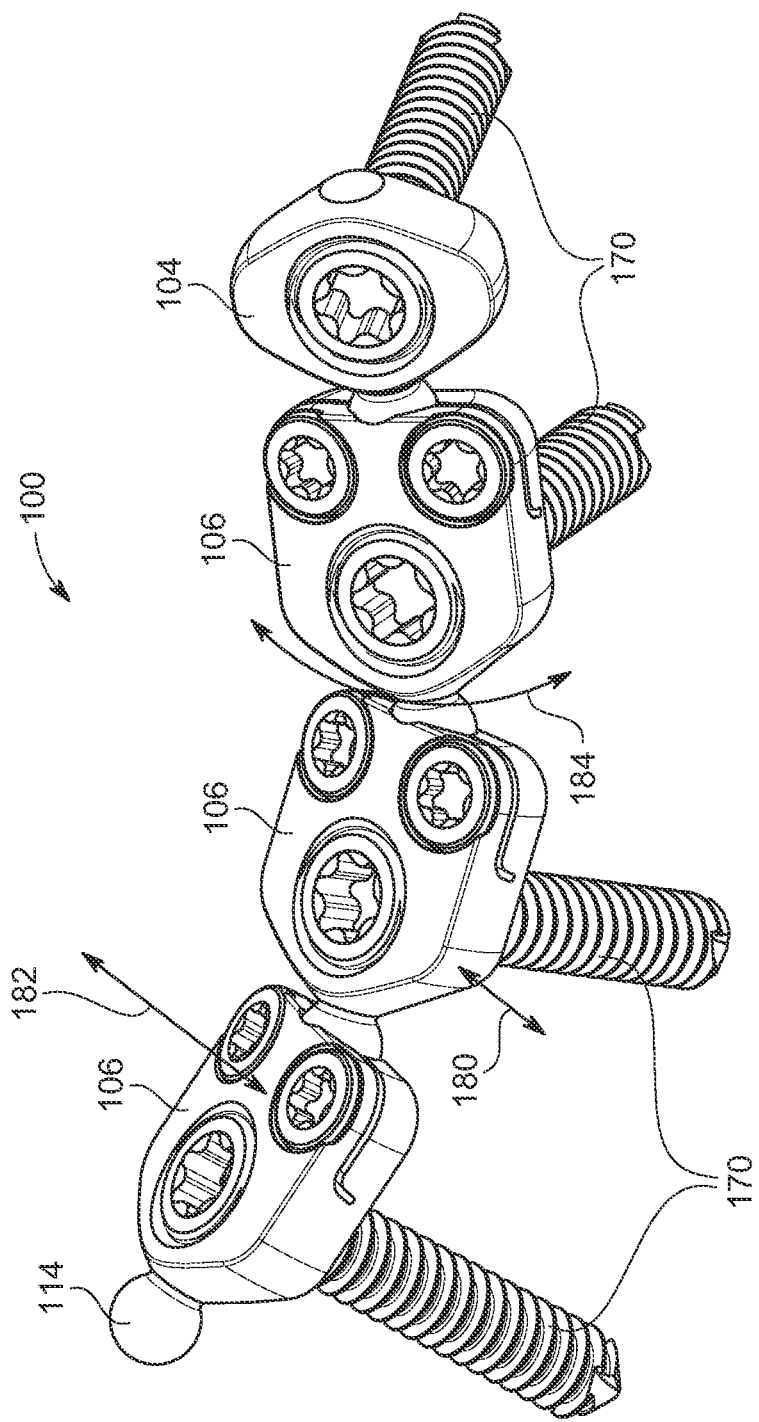
FIG. 2 illustrates a view of the rotation of multiple elements affixed to each other of the self-contouring plate.

Referring to FIG. 2, a view of the rotation of multiple elements affixed to each other of the self-contouring plate is shown.

The self-contouring plate system 100 is shown with central plates 106, and tail plate 104. Head plate 102 (see FIG. 1) is omitted to allow a view of head 114, which is part of the attachment system between the individual plates, allowing the plates to move with respect to each other. Specifically, each element can rotate in three directions—swivel left and right, or yawing 180; tilt forward and backward, or pitching 182; and rotate about its centerline, or rolling 184.

Also shown are bone screws 170, which attach the plates to a patient's bone.

Figure 3:
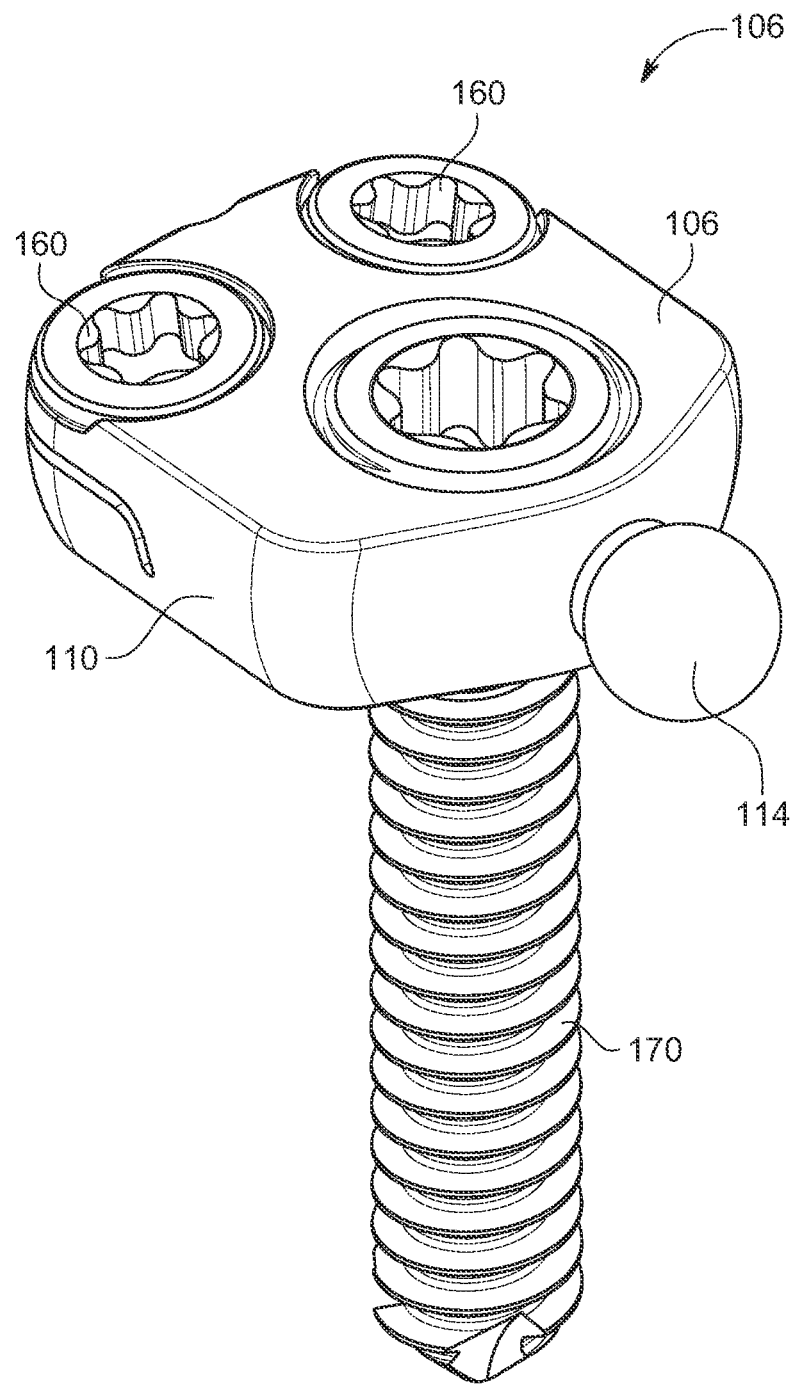
FIG. 3 illustrates a central plate of the self-contouring plate.

Referring to FIG. 3, a central plate of the self-contouring plate is shown.

The central plate 106 is shown including body 110 and head 114. Also shown are two compression screws 160 and one bone screw 170.

Figure 4:
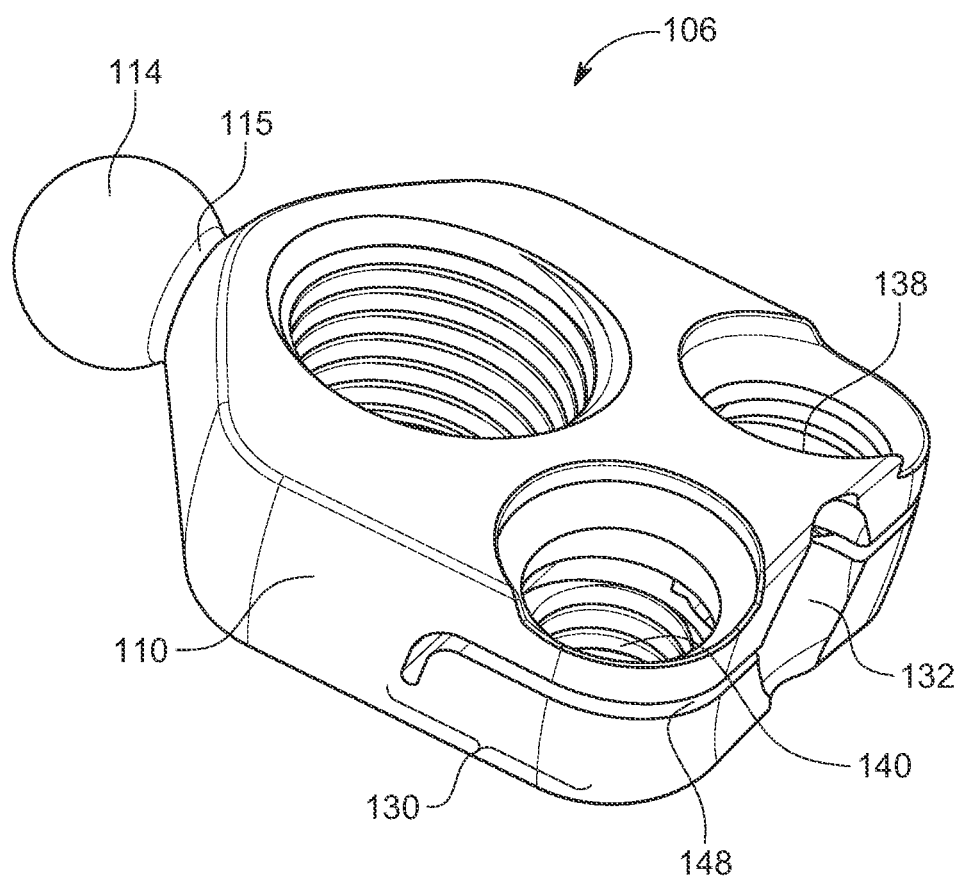
FIG. 4 illustrates an isometric view of the central plate of the self-contouring plate.

Referring to FIG. 4, an isometric view of the central plate of the self-contouring plate is shown.

The central plate 106 includes body 110 that meets head 114 at neck 115. Neck 115 is a smaller diameter than head 114, permitting further rotation of elements attached to the central plate 106. See FIG. 2 as an example.

By varying the length of the neck 115, additional distance can be created between adjacent plates. The additional distance can allow for greater angular deviation of adjacent plates with respect to each other Fixation of elements, or plates, with respect to each other is accomplished by compression of the socket 132 around a head 114.

Using compression screws 160 (see FIG. 3) within first compression hole 138 and second compression hole 140, compression gap 148 is closed, reducing the size of socket 132 and affixing head 114 in place.

Figure 5:
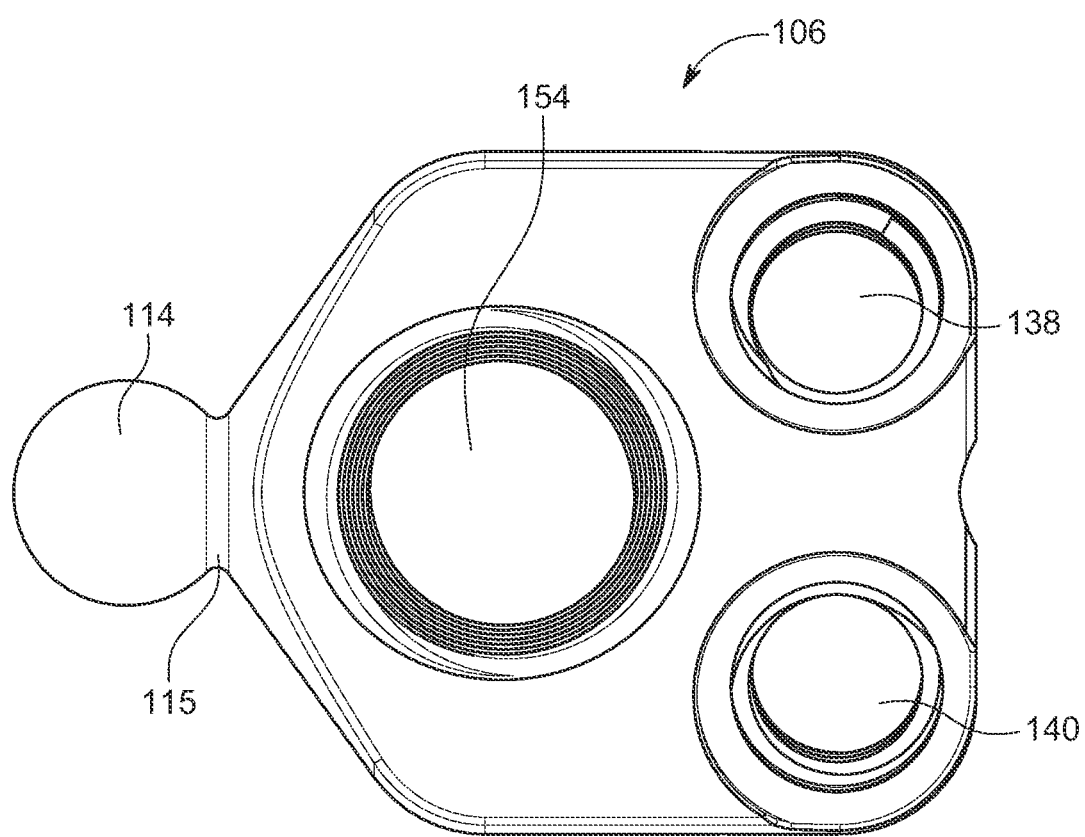
FIG. 5 illustrates a top view of the central plate of the self-contouring plate.
Figure 6:
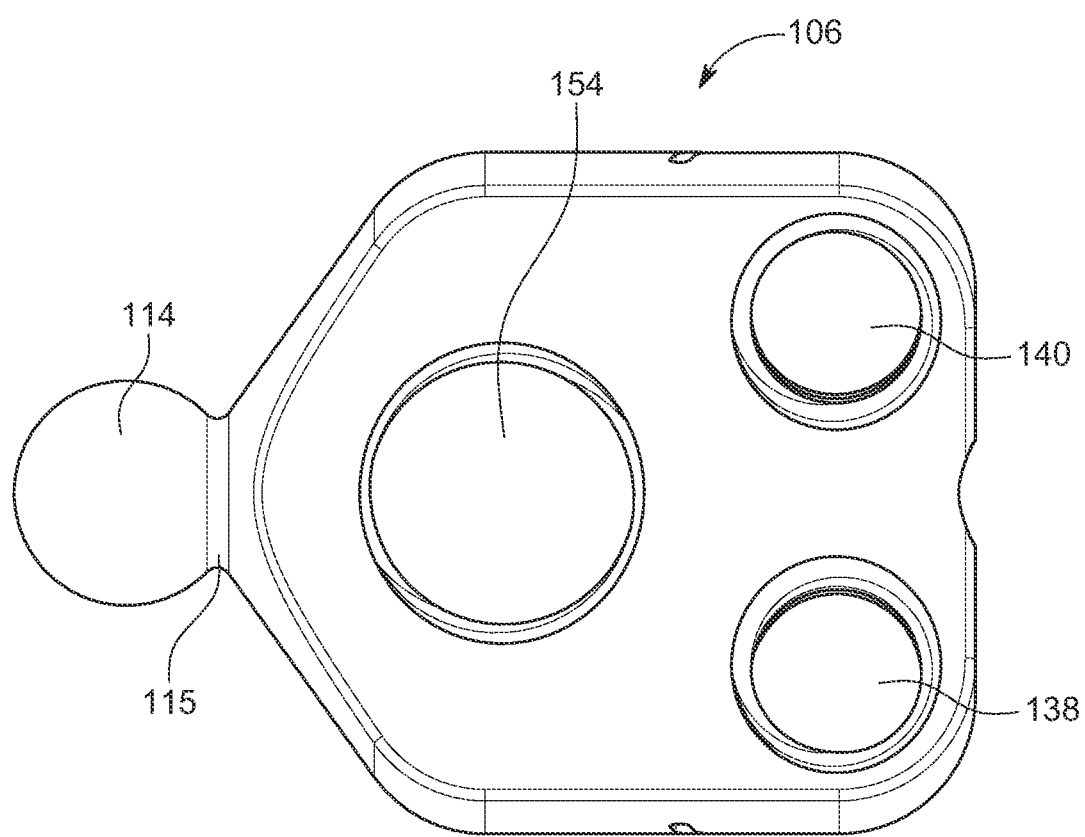
FIG. 6 illustrates a bottom view of the central plate of the self-contouring plate.

Referring to FIGS. 5 and 6, a top view and a bottom view of the central plate of the self-contouring plate are shown.

The central plate 106 is shown with head 114, neck 115, body hole 154, first compression hole 138, and second compression hole 140.

Figure 7:
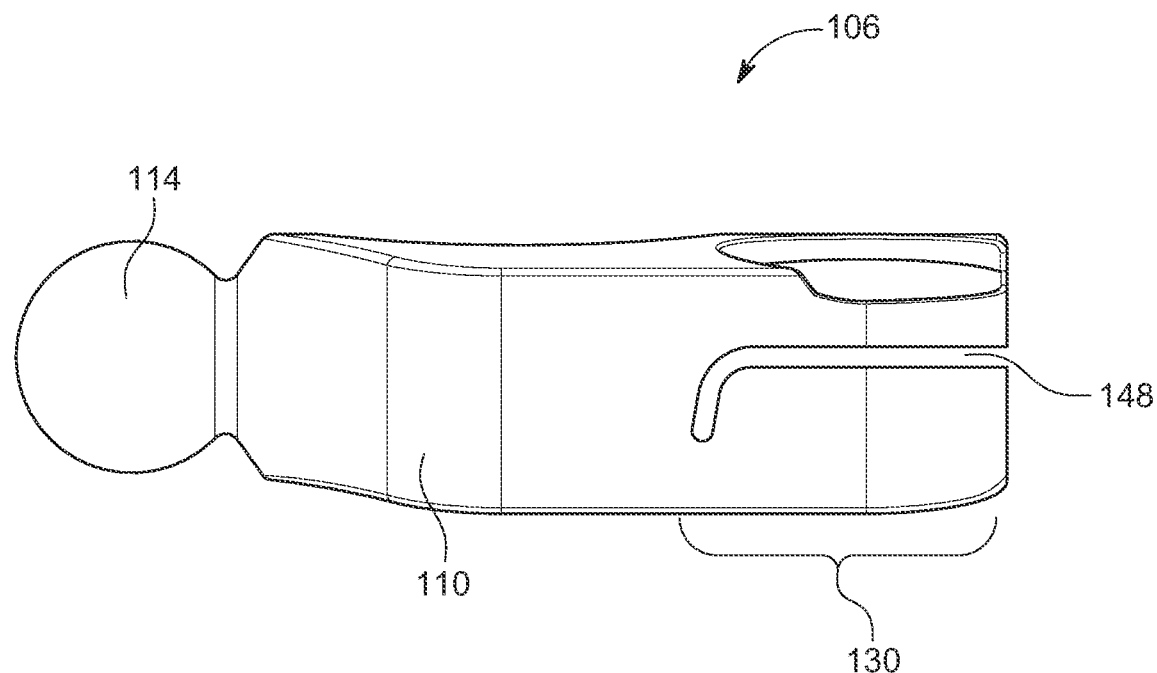
FIG. 7 illustrates a side view of the central plate of the self-contouring plate.
Figure 8:
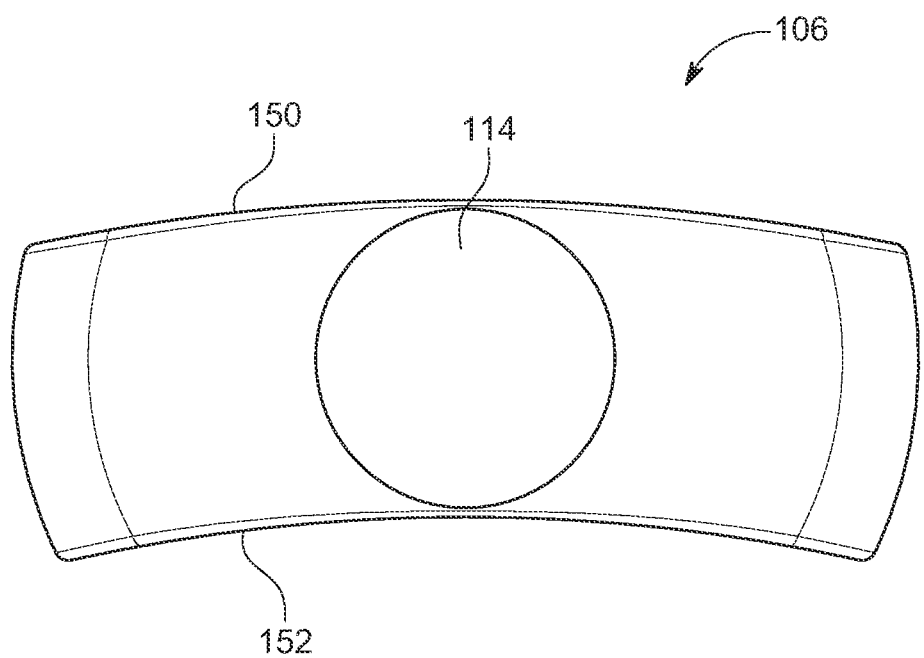
FIG. 8 illustrates a front view of the central plate of the self-contouring plate.

Referring to FIGS. 7 and 8, a side view and a front view of the central plate of the self-contouring plate are shown.

The central plate 106 is shown with head 114, body 110, and compression section 130 including compression gap 148.

Also shown is upper curvature 150 and lower curvature 152. The plates, including the central plate 106, are optionally curved to better match the surface contours of the bone to which they will be affixed. By increasing the surface contact area, the plates better resist rotation and reduce fracture movement.

Figure 9:
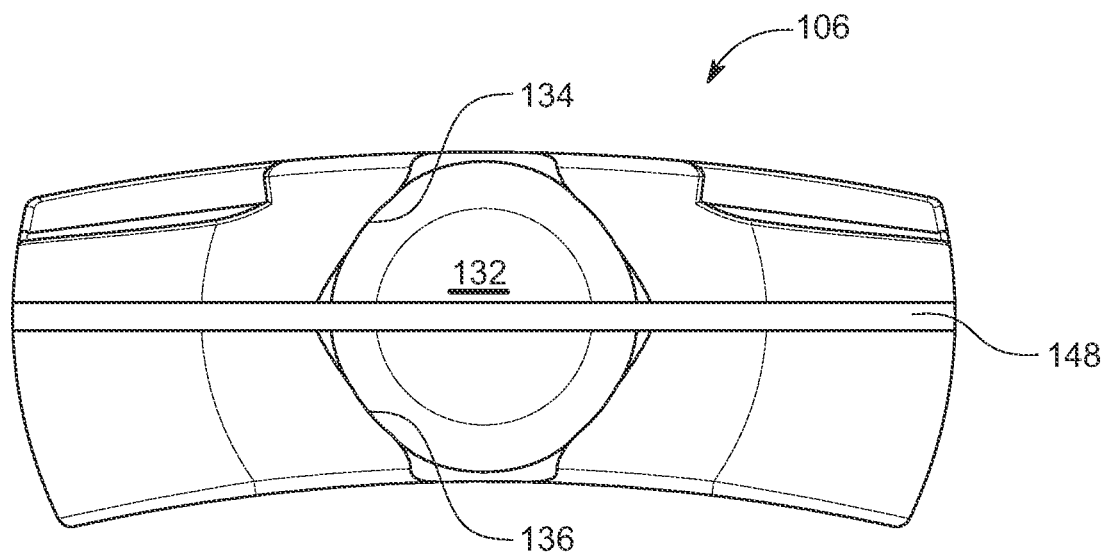
FIG. 9 illustrates a rear view of the central plate of the self-contouring plate.

Referring to FIG. 9, a rear view of the central plate of the self-contouring plate is shown.

The socket 132 is formed from upper cup 134 and lower cup 136. When compressed for fixation, the compression gap 148 reduces, bringing the upper cup 134 closer to the lower cup 136 and compressing the head 114 (see FIG. 3).

Figure 10:
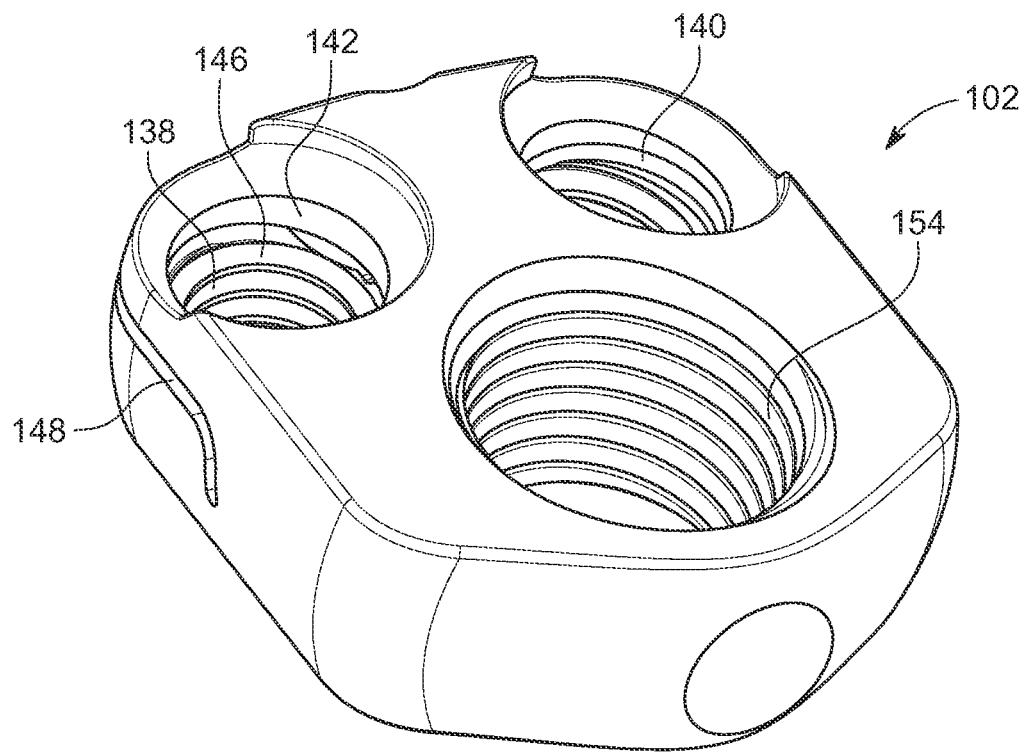
FIG. 10 illustrates an isometric view of the head plate of the self-contouring plate.

Referring to FIG. 10, an isometric view of the head plate of the self-contouring plate is shown.

The headplate 102 includes a first compression hole 138 and a second compression hole 140. Each compression hole 138/140 includes and unthreaded upper section 142 and a threaded lower section 146. This allows the compression screw 160 (see FIG. 3) to thread into the threaded lower section 146, closing the compression gap 148 and reducing the size of the socket 132 (see FIG. 9).

Figure 11:
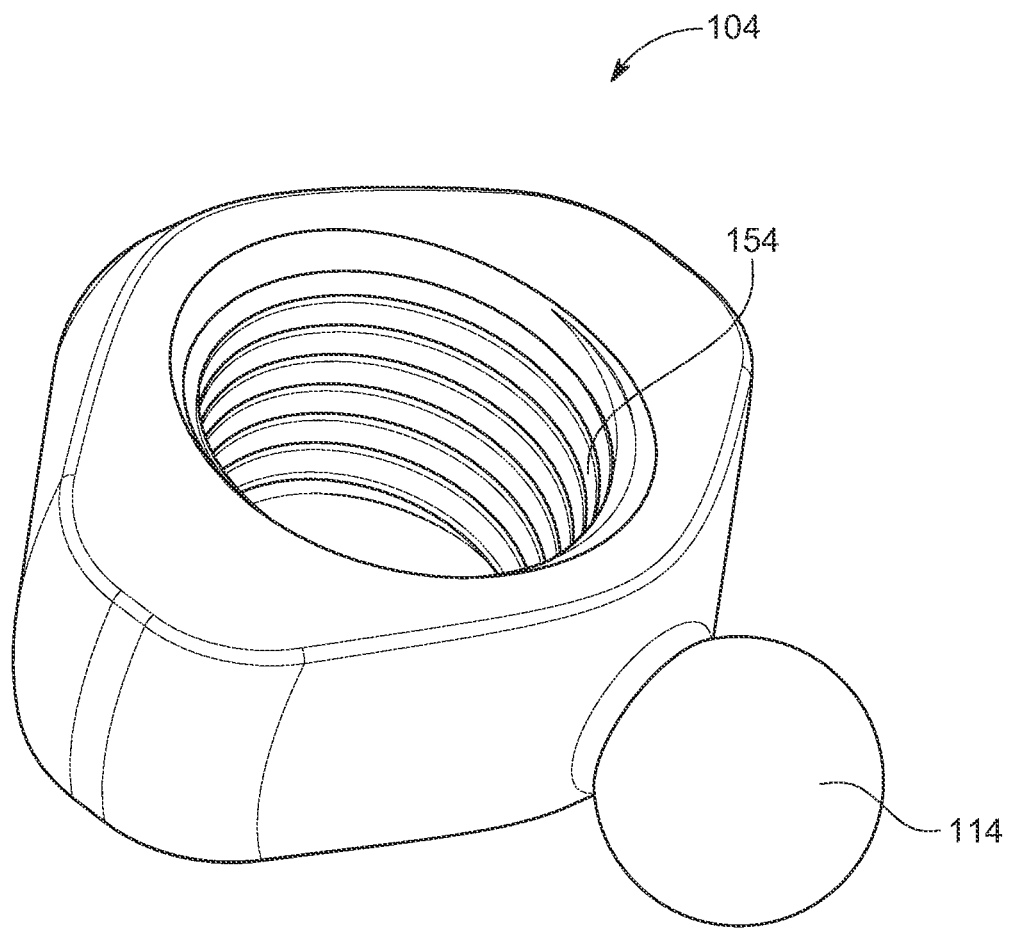
FIG. 11 illustrates an isometric view of the tail plate of the self-contouring plate.

Referring to FIG. 11, an isometric view of the tail plate of the self-contouring plate is shown.

The tail plate 104 includes a body hole 154 and head 114. A socket 132 is unnecessary (see FIG. 9) because the tail plate 104 forms the end of the self-contouring plate system 100, requiring only head 114 to attach to the next element of the system.

Figure 12:
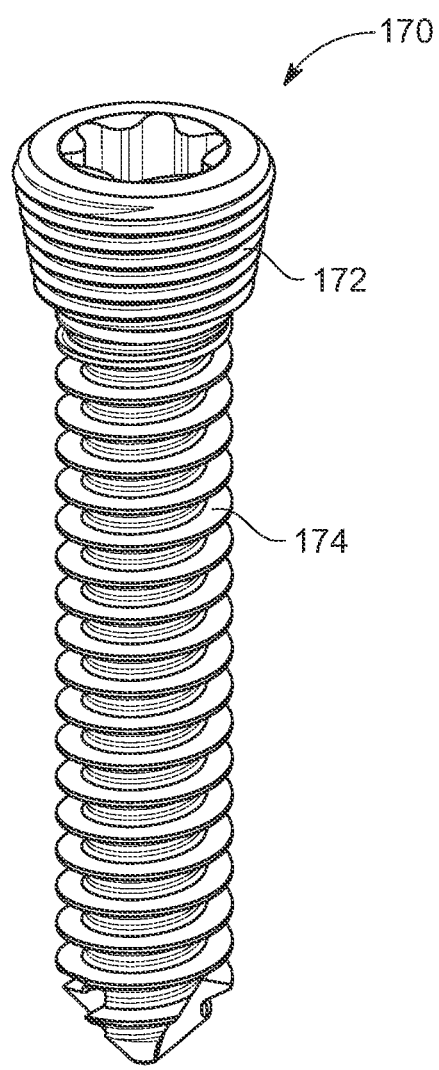
FIG. 12 illustrates an isometric view of an example bone screw of the self-contouring plate.

Referring to FIG. 12, an isometric view of a sample bone screw of the self-contouring plate is shown.

The bone screw 170 includes two threaded sections: a machine thread 172 for interfacing with, for example, head plate 102, and bone thread 174 to interface with the patient's bone.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device adapted to connect across a bone fracture, the device flexible for positioning and then rigid for support, the device comprising:
   a multiplicity of individual plates connecting at ball and socket joints;
     each ball and socket joint allowing for rotation of the individual plates with respect to each other;
     the ball and socket joints each formed from a ball and a socket;
       the ball and the socket located at opposite ends of a body;
       the socket having a compressed position and an uncompressed position;

the ball able to rotate within the socket when the socket is in the uncompressed position;
the ball unable to rotate within the socket when the socket is in the compressed position;
a first compression screw located adjacent to the socket;
wherein tightening the first compression screw puts the socket in the compressed position, and loosening the first compression screw puts the socket in the uncompressed position;
whereby a surgeon can position the device, adjust a position of the multiplicity of individual plates, and fix the position of the multiplicity of individual plates before placing against a bone.

2. The device adapted to connect across a bone fracture of claim 1, further comprising:
a second compression screw;
the second compression screw located opposite the first compression screw, across the socket;
wherein a combination of the first compression screw and the second compression screw determines whether the socket is in the compressed position or the uncompressed position.

3. The device adapted to connect across a bone fracture of claim 1, wherein:
the first compression screw does not pass through the ball, and
the ball is solid.

4. The device adapted to connect across a bone fracture of claim 1, wherein:
a lower surface of the multiplicity of individual plates is curved to match a surface profile of a curved bone.

5. The device adapted to connect across a bone fracture of claim 1, wherein:
the socket is split by a compression gap;
the compression gap opening and closing depending upon whether the socket is in the compressed position or in the uncompressed position.

6. The device adapted to connect across a bone fracture of claim 1, further comprising:
a head plate;
the head plate including a socket, but lacking a ball;
the head plate for placement at a first end of the multiplicity of individual plates.

7. The device adapted to connect across a bone fracture of claim 1, further comprising:
a tail plate;
the tail plate including a ball, but lacking a socket;
the tail plate for placement at a second end of the multiplicity of individual plates.

8. A device to bridge a fracture of a curved bone, the device comprising:
a first plate, a second plate, and a third plate;
the first plate, the second plate, and the third plate each formed from:
a body;
a head connected to the body by a neck;
a socket;
the socket having a compressed position and an uncompressed position;
the first plate, the second plate, and the third plate affixed to each other by interaction of the head in the socket of adjacent plates;
the socket placed in the uncompressed position to allow each plate to be oriented;
the socket placed in the compressed position to fix each plate with respect to its adjacent plate;
a first compression screw;
a second compression screw;
the first compression screw and the second compression screw located on opposite sides of the socket;
wherein a combination of the first compression screw and the second compression screw determines whether the socket is in the compressed position or the uncompressed position; and
whereby a user can loosely connect the first plate, the second plate, and the third plate, position the device against the curved bone, and then secure positions of the first plate, the second plate, and the third plate.

9. The device to bridge a fracture of a curved bone of claim 8, wherein:
the first compression screw does not pass through the head, and the head is solid.

10. The device to bridge a fracture of a curved bone of claim 8, wherein:
a lower surface of the first plate, the second plate, and the third plate is curved to match a surface profile of the curved bone.

11. The device to bridge a fracture of a curved bone of claim 8, wherein:
the socket is split by a compression gap;
the compression gap opening and closing depending upon whether the socket is in the compressed position or in the uncompressed position.

12. The device to bridge a fracture of a curved bone of claim 8, further comprising:
a head plate;
the head plate including a socket, but lacking a ball;
the head plate for placement at a first end of a combination of the first plate, the second plate, and the third plate.

13. The device to bridge a fracture of a curved bone of claim 8, further comprising:
a tail plate;
the tail plate including a ball, but lacking a socket;
the tail plate for placement at a second end of a combination of the first plate, the second plate, and the third plate.

14. A device to bridge a bone fracture of a curved bone, the device comprising:
a plurality of rigid elements;
each element of the plurality of rigid elements including:
a body;
the body including a hole for a bone screw;
a socket within a first end of the body;
a ball-shaped head at a second end of the body;
the ball-shaped head sharing a centerline with the body;
the ball-shaped head able to be movably interfaced with the socket of an adjacent rigid element of the plurality of rigid elements;
the ball-shaped head having an unlocked condition with respect to the socket, and the ball-shaped head having a locked condition with respect to the socket;
a neck;
the neck joining the body to the ball-shaped head;
a first compression screw;
a second compression screw;
the first compression screw and the second compression screw located on opposite sides of the socket;

wherein a combination of the first compression screw and the second compression screw determines whether the socket is in a compressed position or an uncompressed position; and the plurality of rigid elements joined by the ball-shaped heads, allowing each element of the plurality of rigid elements to have six degrees of rotational freedom with respect to each other.

15. The device to bridge a bone fracture of a curved bone of claim 14, wherein:

the first compression screw does not pass through the ball-shaped head, and the ball-shaped head is solid.

16. The device to bridge a bone fracture of a curved bone of claim 14, wherein:

the socket is split by a compression gap;

the compression gap opening and closing depending upon whether the socket is in the compressed position or in the uncompressed position.

17. The device to bridge a bone fracture of a curved bone of claim 14, further comprising:

a head plate;

the head plate including a socket, but lacking a ball;

the head plate for placement at a first end of the plurality of rigid elements.

18. The device to bridge a bone fracture of a curved bone of claim 14, further comprising:

a tail plate;

the tail plate including a ball, but lacking a socket;

the tail plate for placement at a second end of the plurality of rigid elements.

* * * * *